United States Patent
Aggerholm

(10) Patent No.: US 8,021,409 B2
(45) Date of Patent: Sep. 20, 2011

(54) DEPLOYMENT CATHETER

(75) Inventor: Steen Aggerholm, St. Heddinge (DK)

(73) Assignee: Cook Medical Technologies, LLC, Bloomington, IN (US)

(*) Notice: Subject to any disclaimer, the term of this patent is extended or adjusted under 35 U.S.C. 154(b) by 132 days.

(21) Appl. No.: 12/317,355

(22) Filed: Dec. 22, 2008

(65) Prior Publication Data

US 2009/0177260 A1 Jul. 9, 2009

Related U.S. Application Data

(60) Provisional application No. 61/009,099, filed on Dec. 26, 2007.

(51) Int. Cl.
*A61F 2/84* (2006.01)
(52) U.S. Cl. .................. 623/1.11; 606/108
(58) Field of Classification Search .......... 600/128, 600/130, 139–141, 144; 604/103.04, 103.09; 606/108, 192, 194; 623/1.11, 1.12, 1.23
See application file for complete search history.

(56) References Cited

U.S. PATENT DOCUMENTS

| | | | |
|---|---|---|---|
| 5,308,342 A | 5/1994 | Sepetka et al. | |
| 5,484,424 A * | 1/1996 | Cottenceau et al. | 604/525 |
| 5,605,543 A * | 2/1997 | Swanson | 604/102.02 |
| 5,658,251 A | 8/1997 | Ressemann et al. | |
| 5,743,876 A | 4/1998 | Swanson | |
| 5,976,120 A | 11/1999 | Chow et al. | |
| 6,066,114 A * | 5/2000 | Goodin et al. | 604/103.04 |
| 6,746,423 B1 | 6/2004 | Wantink | |
| 2003/0065352 A1 | 4/2003 | Yang et al. | |
| 2005/0209582 A1 | 9/2005 | Quinn et al. | |
| 2007/0010786 A1 | 1/2007 | Casey et al. | |

OTHER PUBLICATIONS

PCTUS2008087958, May 28, 2009, International Search Report.
PCTUS2008087958, May 28, 2009, Written Opinion.

* cited by examiner

*Primary Examiner* — Ryan Severson
(74) *Attorney, Agent, or Firm* — Brinks Hofer Gilson & Lione

(57) ABSTRACT

An inner catheter (36) for use in an endoluminal delivery assembly (10) includes a stiffening element positioned at a transition between a hypotube (36a), a middle tube (36b) and a distal tube (36c) of the inner catheter (36) having different flexibilities. The stiffening element comprises three stiffening wires (42) embedded within the internal wall of the inner catheter (36) at their proximal ends. The stiffening wires (42) extend inwardly and distally to meet at an apex (60).

12 Claims, 4 Drawing Sheets

DEPLOYMENT CATHETER

CROSS-REFERENCE TO RELATED APPLICATIONS

This application claims priority of provisional application Ser. No. 61/009,099, filed Dec. 26, 2007.

TECHNICAL FIELD

The present invention relates to an introducer or a deployment assembly for example for deploying an implant or other prosthesis within a patient, and in particular to the catheter or cannula that carries the implant or other prosthesis.

BACKGROUND OF THE INVENTION

Catheters have found widespread use in medical procedures, such as percutaneous transluminal coronary angioplasty (PTCA) or for delivery of stents. A typical endoluminal deployment system includes an inner catheter or cannula, which may also be arranged as a pusher and/or dilator (hereinafter referred to as an inner catheter) and a sheath covering the inner catheter. An implant or prosthesis is carried on the inner catheter and is fixed thereto by means of the covering sheath, with or without one or more restraining wires or any of a number of other known retention systems.

The implant or prosthesis might be a stent, a stent graft, a filter, an occlusion device or any other implantable device of such a nature.

Most catheters are guided to the application site by sliding the catheter along a guide wire, which has been carefully advanced and arranged within the patient. During advancement of the catheter along the guide wire, it is important to keep the guide wire steady. Ordinary catheters are guided to the application site in a patient by sliding the catheter along a guide wire extending all the way through a lumen of the catheter from the proximal end to the distal end thereof. To enable the physician to hold or manipulate the guide wire during advancement of the catheter along the guide wire, it is necessary to have an excess length of guide wire. The guide wire must hence have a length of about twice the length of the catheter, e.g. 3 m in total, which greatly impedes the procedure. An important sub-category of catheters are catheters of the so-called rapid exchange type, which greatly facilitate operation, especially exchange of catheters if it is found during a procedure that a different kind or size of catheter is needed for the specific purpose. In the rapid exchange catheter, the guide wire only passes through a minor part of the catheter at the distal end thereof, whereas along a majority of the catheter, the guide wire runs in parallel with the catheter. Hence it is not necessary to have an excess length of guide wire.

Once the distal end of the inner catheter has been positioned inside a patient, typically at the site of the patient's vasculature to be treated, the device is released and deployed in the desired position. The deployment operation involves retracting the covering sheath so as to expose the device to be implanted, which device is then deployed, either by self-expansion or by means of an expansion device such as an inflatable balloon located internally of the device. In the case where the device is also held by restraining wires, these are withdrawn, typically after retraction of the sheath. Restraining wires may or may not be used in such apparatus, generally depending upon the nature of the device to be deployed, size restrictions and the particular medical application or intervention procedure.

An important feature of catheters is the transmission of force, the so-called push force, from the proximal end to the distal end of the catheter. This transmission significantly affects the physician's ability to direct the distal end of the catheter into a body lumen of a patient by manipulating the proximal end thereof. Another important feature of catheters is the flexibility of the distal end to bend and conform to the body lumen wall without causing any injury to the lumen wall. Hence catheters, especially of the rapid exchange type, are commonly manufactured of a metal proximal shaft portion of relatively stiffness, and a relatively flexible plastics distal portion bonded to the metal shaft portion. An abrupt change of properties between the shaft portion and the distal portion however increases the risk of twist and kinking. Hence there is a need to provide a good transition between the relatively stiff proximal section to the relatively more flexible distal section to provide a sufficient resistance to twist and kinking while maintaining flexibility and ability to bend.

A problem with this type of arrangement is that kinking can occur at the transition between the portions having different flexibilities. This kinking can result in closure of the lumen of the catheter. In order to control the flexibility, some inner catheters are provided with a wire fixed to the internal surface of the inner catheter at the point where the two parts having differing flexibility are connected. This is illustrated in FIG. 1. However, whilst the wire provides a stiffening function, it results in an uneven distribution of flexibilities in the radial direction of the inner catheter.

Other examples of stiffening members are disclosed in U.S. Pat. No. 5,658,251, U.S. Pat. No. 6,066,114 and U.S. Pat. No. 6,746,423.

US 2007/0010786 discloses a catheter suitable for advancement through a body passageway of a patient. The catheter comprises a catheter body which is flexible to provide the necessary trackability for the catheter to advance through a body passageway, and two stainless steel reinforcement wires extending along the catheter body which provide the necessary pushability to advance the catheter through the passageway. The reinforcements are positioned diametrically opposed to one another by approximately 180 degrees on opposite sides of the longitudinal axis of the catheter, and the catheter body is relatively soft and twistable. This configuration enables the entire catheter to twist spontaneously during advancement so that the reinforcements orientate themselves along a plane of neutral bending during advancement of the catheter.

Kinking between portions of differing flexibility is particularly problematic for a rapid exchange balloon catheter.

SUMMARY OF THE INVENTION

The present invention seeks to provide an improved deployment assembly and an improved inner catheter or cannula.

According to a first aspect of the present invention, there is provided a deployment catheter for carrying a device to implanted in a patient, including at least two longitudinal portions having different flexibilities, the catheter including a plurality of stiffening elements substantially evenly spaced radially around the catheter at a transition between the two portions.

Spacing a plurality of stiffening elements substantially evenly around the catheter provides a more even transition in flexure in all radial directions of the catheter.

Preferably at least three stiffening elements are provided. In preferred embodiments an odd number of stiffening elements is provided.

The longitudinal portions may include a hypotube, a middle tube and a distal tube.

In an embodiment, the proximal end of the stiffening elements is located at a junction between the hypotube and the middle tube. The distal end of the stiffening element may be found within the distal tube.

The stiffening elements are preferably fixed to the inside wall of the catheter, and most preferably at one of their ends. In a particularly preferred embodiment, the stiffening elements are embedded within the wall of the catheter at least at their proximal end.

The stiffening elements are preferably connected to one another within a lumen of the catheter. This allows the stiffening elements to be smaller and thus usable in smaller catheters. The stiffening elements may meet at a point located substantially centrally within the lumen.

The stiffening elements may extend radially inwardly and distally of a point at which they are attached to the catheter.

According to a second aspect of the present invention, there is provided a rapid exchange balloon catheter for carrying a device to be implanted in a patient, including a hypotube, a middle tube and a distal tube, the catheter including a plurality of stiffening elements located at a junction between the hypotube and the middle tube, wherein an odd number of stiffening elements is provided, and wherein the stiffening elements extend radially inwardly and distally of a point at which the stiffening elements are attached to the catheter.

According to a third aspect of the present invention, there is provided a delivery system including a deployment catheter as specified herein and a device to be deployed in a patient.

Preferably, the device is a stent, a stent graft, a filter or an occlusion device.

BRIEF DESCRIPTION OF THE DRAWING

Embodiments of the present invention are described below, by way only, with reference to the accompanying drawings, in which.

DETAILED DESCRIPTION

It is to be understood that the Figures are schematic and do not show the various components to their actual scale. In many instances, the Figures show scaled up components to assist the reader.

In this description, when referring to a deployment assembly, the term distal is used to refer to an end of a component which in use is furthest from the surgeon during the medical procedure, including within a patient. The term proximal is used to refer to an end of a component closest to the surgeon and in practice in or adjacent an external manipulation part of the deployment of treatment apparatus.

On the other hand, when referring to an implant such as a stent or stent graft, the term proximal refers to a location which in use is closest to the patient's heart, in the case of a vascular implant, and the term distal refers to a location furthest from the patient's heart.

Figure 2:
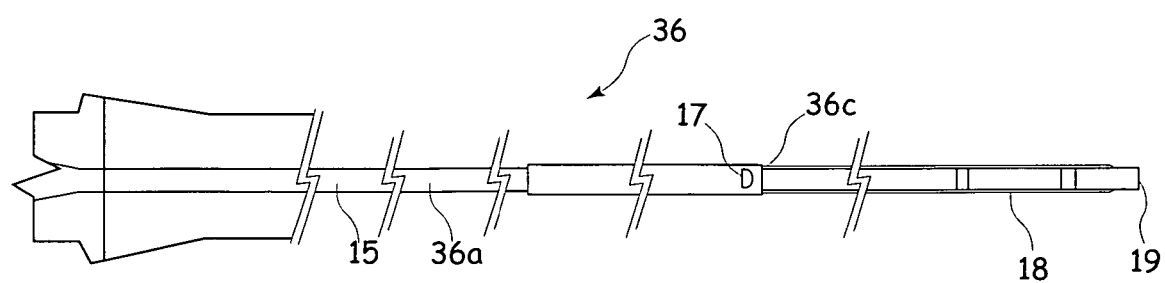
FIG. 2 shows a side view of a catheter that may be used with embodiments of the present invention.

In FIG. 2 is shown a catheter that may be used with embodiments of the invention. This Figure is somewhat distorted for illustration purposes, as the total length of the catheter is about 140 cm. The catheter 36 has a proximal end and a distal end. The catheter 36 comprises tubular metal shaft body 36a, typically known as a hypotube, and made of a Nitinol alloy. An inflation lumen 15 extends in the full length of the metal shaft body 36. A plastics distal end portion 36c is attached to the end of the tubular metal shaft body 36a by bonding. The plastics distal end portion 36c comprises a side port 17 for a guide wire (not shown) at a proximal side of an inflatable balloon 18, so the guide wire may extend through the most distal part of the catheter to the distal end opening 19.

Figure 3:
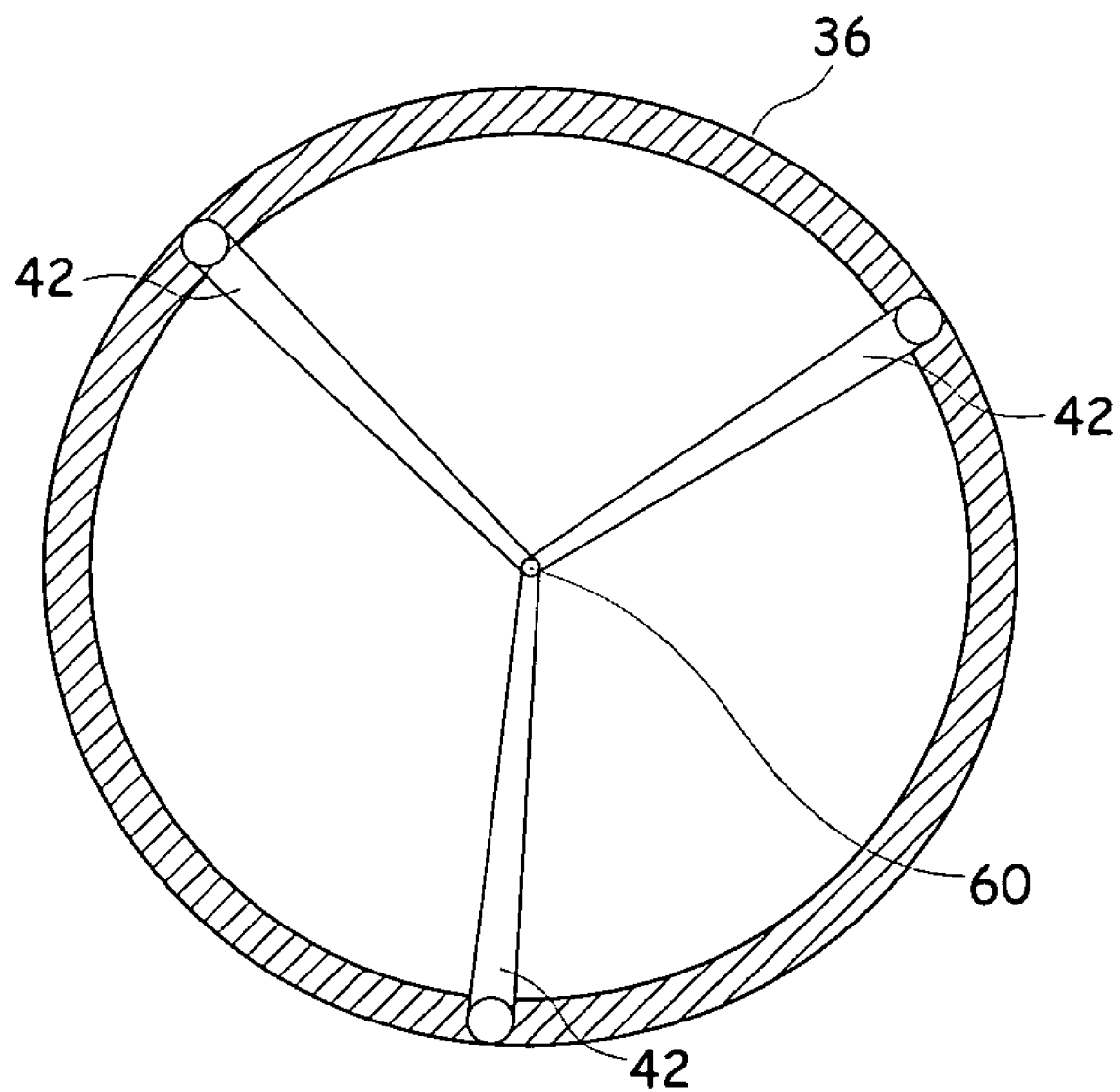
FIG. 3 shows a transverse cross section of a catheter according to an embodiment of the present invention.
Figure 4:
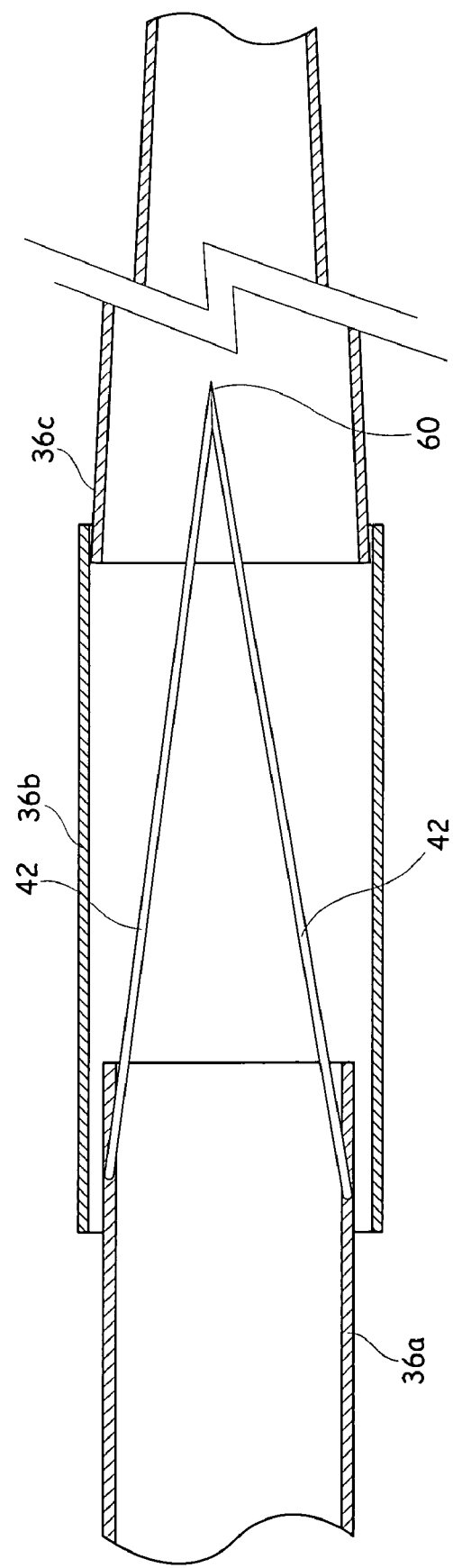
FIG. 4 shows a side view of the inside of the catheter of FIG. 3.
Figure 5:
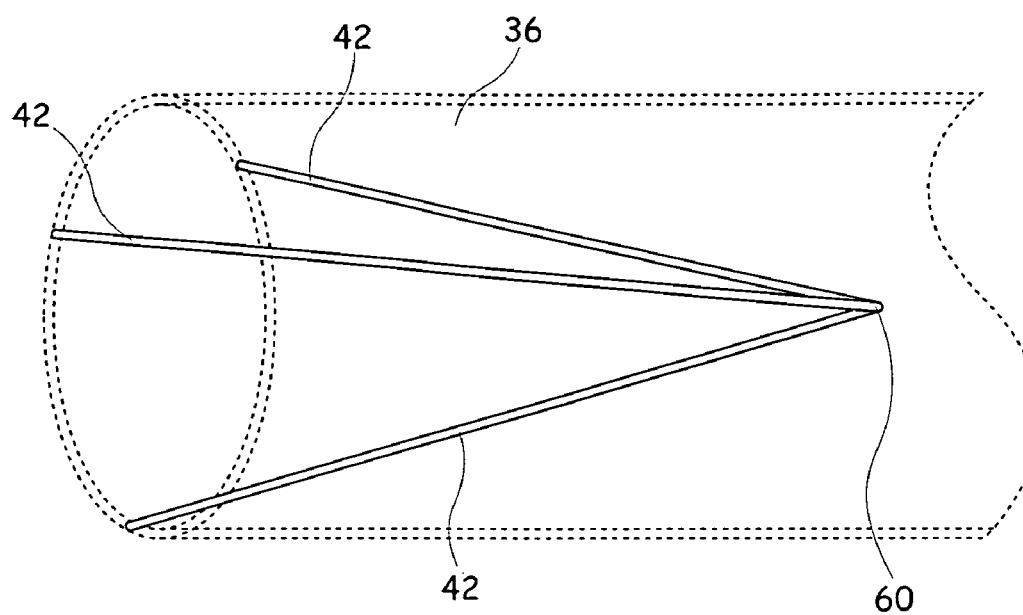
FIG. 5 shows a perspective view of the catheter of FIG. 3.

Referring now to FIGS. 3, 4 and 5, a preferred embodiment of the invention is described. FIGS. 3, 4 and 5 show an inner catheter 36. The inner catheter 36 is made up of three parts arranged longitudinally: a hypotube 36a, a middle tube 36b and a distal tube 36c. The distal tube 36c is relatively flexible to allow the inner catheter 36 to negotiate a patient's vasculature, whereas the hypotube 36a is relatively stiff to facilitate pushing of the inner catheter 36 from the proximal end. The middle tube 36b has a stiffness intermediate that of the distal tube 36c and the hypotube 36a.

Three stiffening elements 42 are provided within the lumen of the inner catheter 36. The stiffening elements are made from a suitable wire, for example a shape memory wire such as nickel titanium (Nitinol). At their proximal end the stiffening elements 42 are embedded within the internal wall of the hypotube 36a. The three stiffening elements 42 are located substantially symmetrically in a radial direction around the inner catheter 36. In other words, they are separated by approximately 120°.

Each stiffening element 42 extends radially inwardly from its attachment point. The three stiffening elements meet at an apex 60 towards the distal end of the inner catheter 36. The positioning of the stiffening elements 42 is such that they extend beyond the distal end of the middle tube 36b and into the proximal end of the distal tube 36c. The apex 60 is thus located within the lumen of the distal tube 36c.

In use, the inner catheter 36 is able to bend as it negotiates a body passageway. As the inner catheter 36 is passed around a bend, the stiffening elements 42 reduce the risk of the inner catheter 36 kinking between a portion of greater flexibility 36c, 36b and a portion of lower flexibility 36a, 36b.

Figure 6:
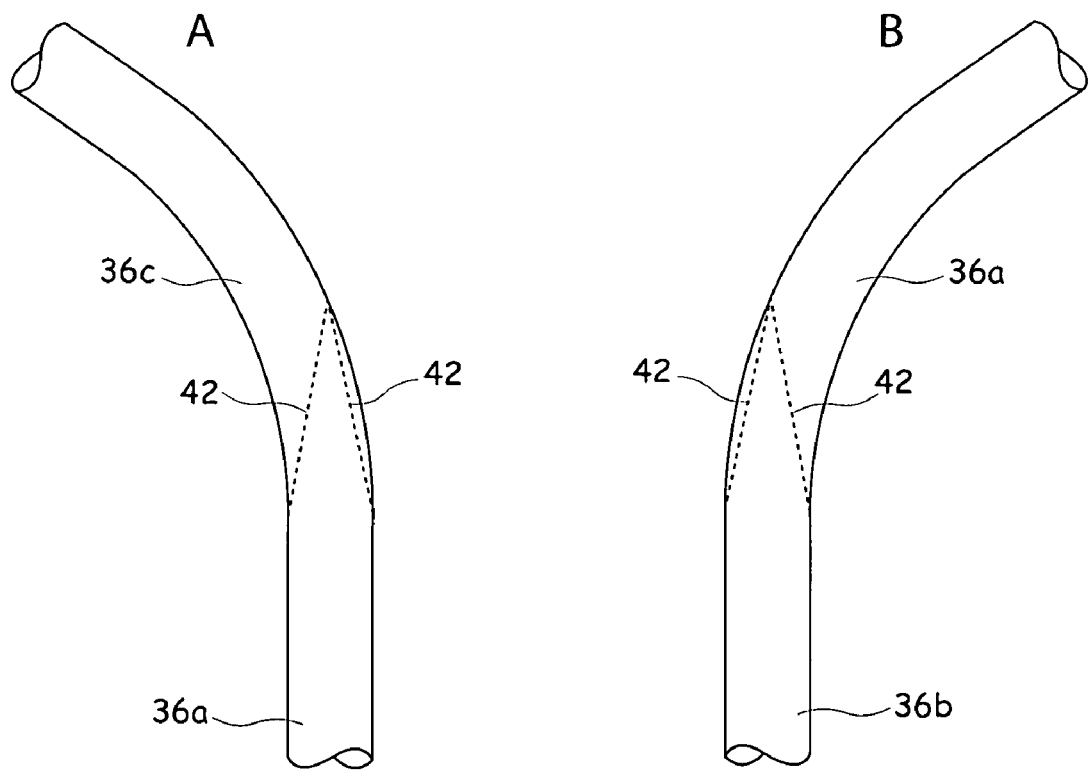
FIG. 6 shows bending of the catheter of FIG. 3.

By having the stiffening elements 42 extend inwardly and distally with respect to the inner catheter 36, the inner catheter 36 is still able to bend to a certain extent in all radial directions (see FIG. 6). By providing the stiffening elements 42 substantially symmetrically radially around the inner catheter 36, the flexibility of the inner catheter 36 is evenly distributed in its radial direction.

Figure 1:
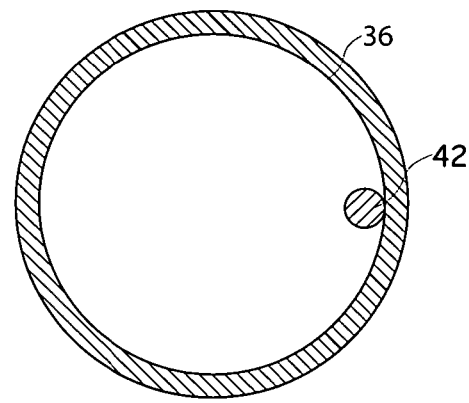
FIG. 1 shows a transverse cross section of a prior art catheter.

The use of a plurality of stiffening wires 42 enables the stiffening wires to be smaller or thinner than in prior art catheters where a single stiffening wire 42 is used (see FIG. 1). This enables the disclosed stiffening element to be used in a catheter 36 having a smaller diameter.

Embedding the proximal ends of the stiffening elements within the internal wall of the hypotube 36a avoids space within the lumen being taken up.

An advantage of the stiffening elements 42 meeting at an apex 60 is that the structure has no effect on the inner catheter 36 until it has flexed sufficiently to allow its inner walls to contact the stiffening elements 42. This is particularly important where the hypotube 36a, the middle tube 36b and the distal tube 36c have been designed to have specific flexibilities. These different portions of the inner catheter 36 thus retain the advantages of their different flexibilities until the inner wall of, for example, the middle tube 36b or the distal tube 36c contacts the apex 60 (see FIG. 6). In other words, the stiffening elements 42 do not interfere with the normal bending and flexing of the inner catheter 36 until the time at which kinking is likely.

In an embodiment, the stiffening elements 42 do not meet at an apex 60, but are aligned with, or embedded within, the inner wall of the inner catheter 36. In such an embodiment, the stiffening element 42 would flex as soon as the middle tube 36b started to bend.

In the above-described embodiment, the stiffening elements 42 are of approximately equal length. However, in some embodiments, the stiffening elements 42 could individually have differing lengths. In such embodiments, the stiffening elements 42 may not meet at a point. Rather, the distal ends of the stiffening elements may remain free within the lumen of the inner catheter 36, but may (in some examples) still extend inwardly towards the centre of the lumen. By providing stiffening elements 42 with varying lengths, the transition and flexibility properties of the catheter 36 can be altered according to requirements.

The skilled person will appreciate that many modifications may be made to the above-described embodiment. Although preferred materials or fabrication are indicated, other suitable materials may be used. Furthermore, stiffening elements may be provided between any two longitudinal portions having differing flexibility and need not extend across a transition between three portions of differing flexibility as described for the preferred embodiment.

Although the preferred embodiments have been described in relation to a rapid exchange balloon catheter, the teachings herein are applicable to other catheter or cannula based delivery systems suitable for delivering stents, stent-grafts, filters, occlusion devices and other implants.

The disclosures in U.S. 61/009,099, from which this application claims priority, and in the abstract accompanying this application are incorporated herein by reference.

What is claimed is:

1. A deployment catheter for carrying a device to be implanted in a patient, including at least a first longitudinal portion and a second longitudinal portion, the first and second longitudinal portions having different flexibilities and a continuous lumen extending therethrough, the catheter including a plurality of stiffening elements substantially evenly spaced radially around the catheter at a transition between the two portions, wherein a first end portion of each stiffening element is attached to a wall of the first longitudinal portion, the wall at least partially defining the lumen of the first longitudinal portion, each stiffening element extending from the first longitudinal portion and into the second longitudinal portion, and wherein a second end portion of each of the stiffening elements is disposed within the lumen and free from attachment to the second longitudinal portion, the second end portion being spaced radially away from the second longitudinal portion when the second longitudinal portion is in a substantially straight configuration relative to the first longitudinal portion, and the second end portions of the stiffening elements are connected to one another within a lumen of the catheter.

2. The deployment catheter of claim 1, including at least three stiffening elements.

3. The deployment catheter of claim 1, including an odd number of stiffening elements.

4. The deployment catheter of claim 1, wherein the longitudinal portions include a hypotube, a middle tube and a distal tube.

5. The deployment catheter of claim 4, wherein the first end portions of the stiffening elements are located at a junction between the hypotube and the middle tube.

6. The deployment catheter of claim 4, wherein the first longitudinal portion is the hypotube and the second longitudinal portion is the distal tube.

7. The deployment catheter of claim 1, wherein the first longitudinal portion is a hypotube and the second longitudinal portion is a middle tube.

8. The deployment catheter of claim 1, wherein the first end portions include at least a proximal end of the stiffening elements and the proximal ends of the stiffening elements are embedded within the wall of the catheter.

9. The deployment catheter of claim 1, wherein the second end portions of the stiffening elements meet at a point located substantially centrally within the lumen.

10. The deployment catheter of claim 1, wherein the catheter is a rapid exchange balloon catheter.

11. A delivery system including the catheter of claim 1, and a device to be implanted in a patient.

12. The delivery system of claim 11, wherein the device is a stent, a stent graft, a filter or an occlusion device.

* * * * *